(12) United States Patent
Battistini et al.

(10) Patent No.: US 6,797,722 B2
(45) Date of Patent: Sep. 28, 2004

(54) USE OF 3-(2-ETHYLPHENYL)-5-(3-METHOXYPHENYL)-1H-1,2,4-TRIAZOLE FOR THE TREATMENT OF AUTOIMMUNE DISEASES

(75) Inventors: Luca Battistini, Rome (IT); Giovanna Borsellino, Rome (IT); Rita De Santis, Pomezia (IT); Paolo Carminati, Pomezia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 24 days.

(21) Appl. No.: 10/137,699

(22) Filed: May 3, 2002

(65) Prior Publication Data

US 2003/0207931 A1 Nov. 6, 2003

(51) Int. Cl.$^7$ ............................................... A61K 31/41
(52) U.S. Cl. .................... 514/383; 514/825; 514/903
(58) Field of Search ........................... 514/383, 825, 514/903

(56) References Cited

U.S. PATENT DOCUMENTS 6,323,230 B1 * 11/2001 Rossi

OTHER PUBLICATIONS

Sustento–Reodica et al, Lancet Jul. 26, 1997 350(9073) 298, abstract.*
Andoh et al, Int J Mol Med May 9, 2002 (5) 499–502, abstract.*
du Haut Champ, Ann Ital Med Int Jan.–Mar. 17, 2002 (1) 11–20, abstract.*
Mistrello et al, Immunopharmacology 1985 10(3) 163–9, abstract.*
Mistrello et al Immunopharmacology, 10 (1985) 163–169 XP–002082252 Immunological Profile of DL111–IT, a New Immunosuppressant Agent.

* cited by examiner

Primary Examiner—Rebecca Cook
(74) Attorney, Agent, or Firm—Nixon & Vanderhye P.C.

(57) ABSTRACT

The present invention discloses a method for treating a subject affected by an autoimmune disease, in particular multiple sclerosis, lupus erythematosus systemicus and reumatoid arthritis, comprising administering to said subject an effective amount of 3-(2-ethylphenyl)-5-(3-methoxyphenyl)-1H-1,2,4-triazole. The present invention further discloses a method for inhibiting γδ T cells in a subject in need thereof, said method comprising administering to said subject an effective amount of the same compound.

6 Claims, 6 Drawing Sheets

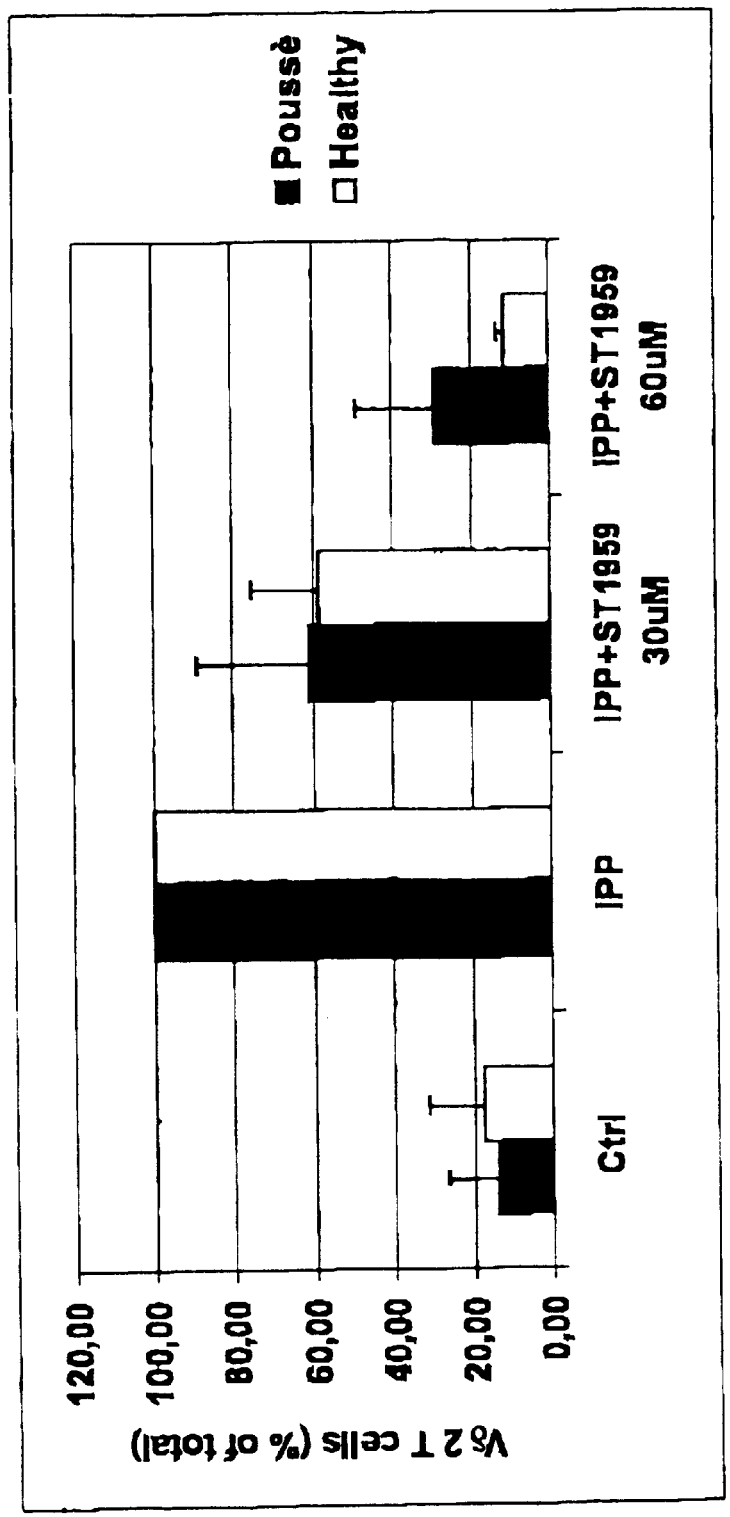
Figure 1: ST1959 inhibits Vδ2 T cell IPP-mediated expansion

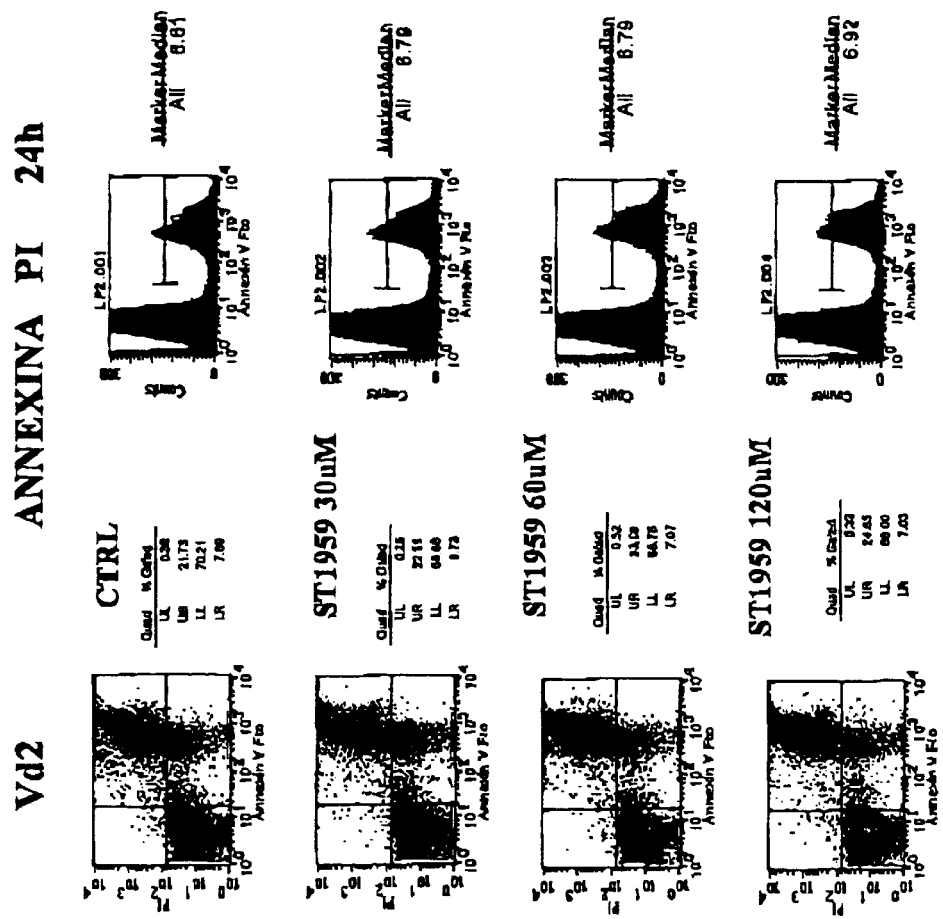
Figure 2: ST1959 does not induce apoptosis in Vδ2 T cells

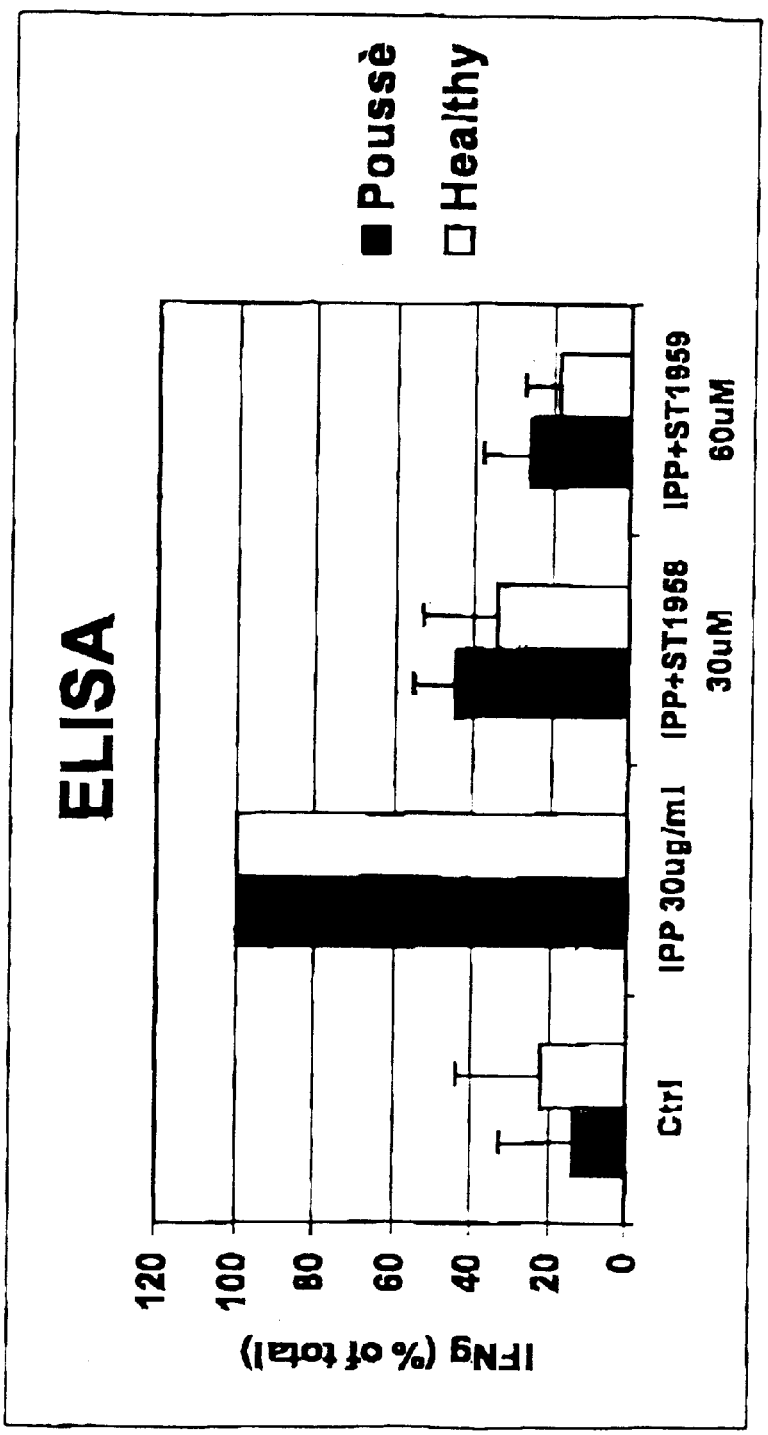
Figure 3: ST1959 inhibits IFNγ release in IPP-stimulated T cells

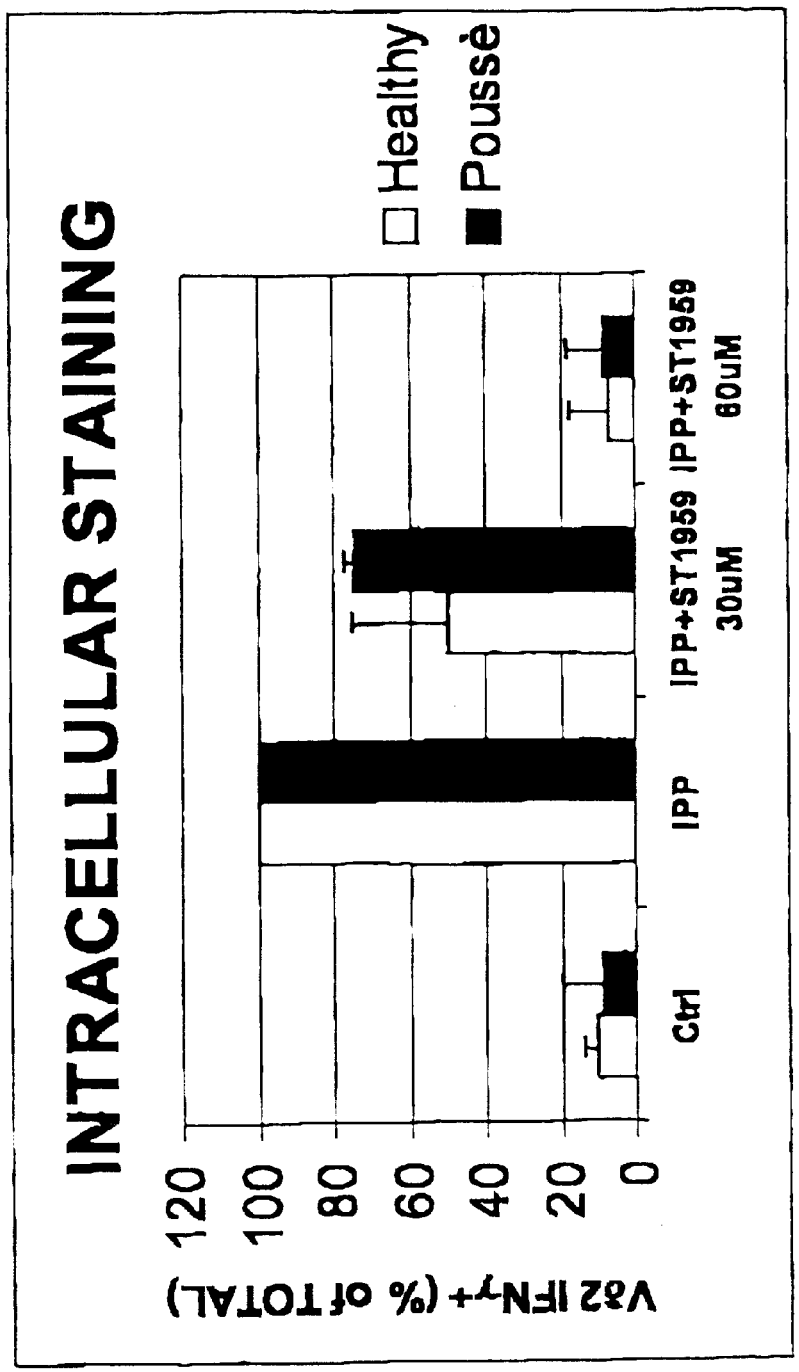
Figure 4: ST1959 inhibits IFNγ producing Vδ2 T cells

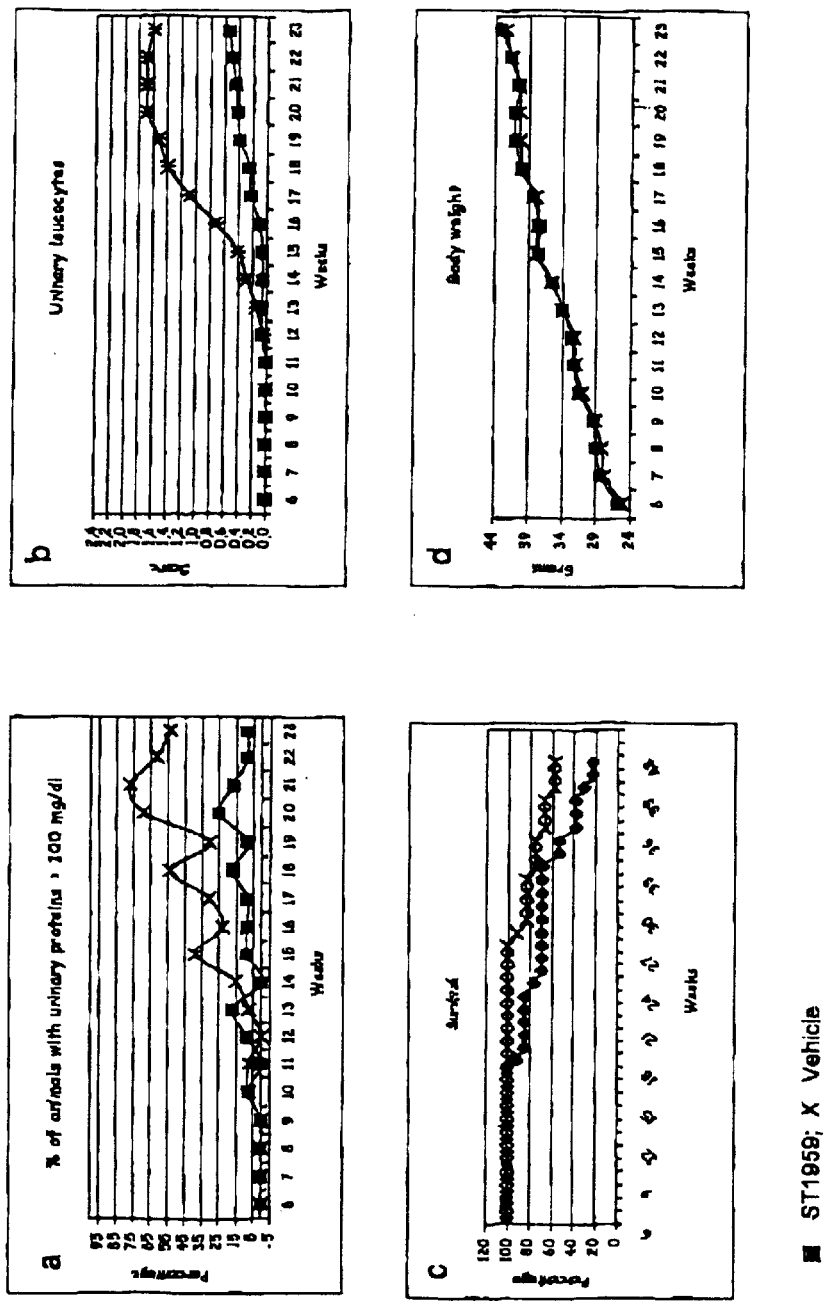
Figure 5: ST1959 controls renal damage and improves survival in a mouse LES model

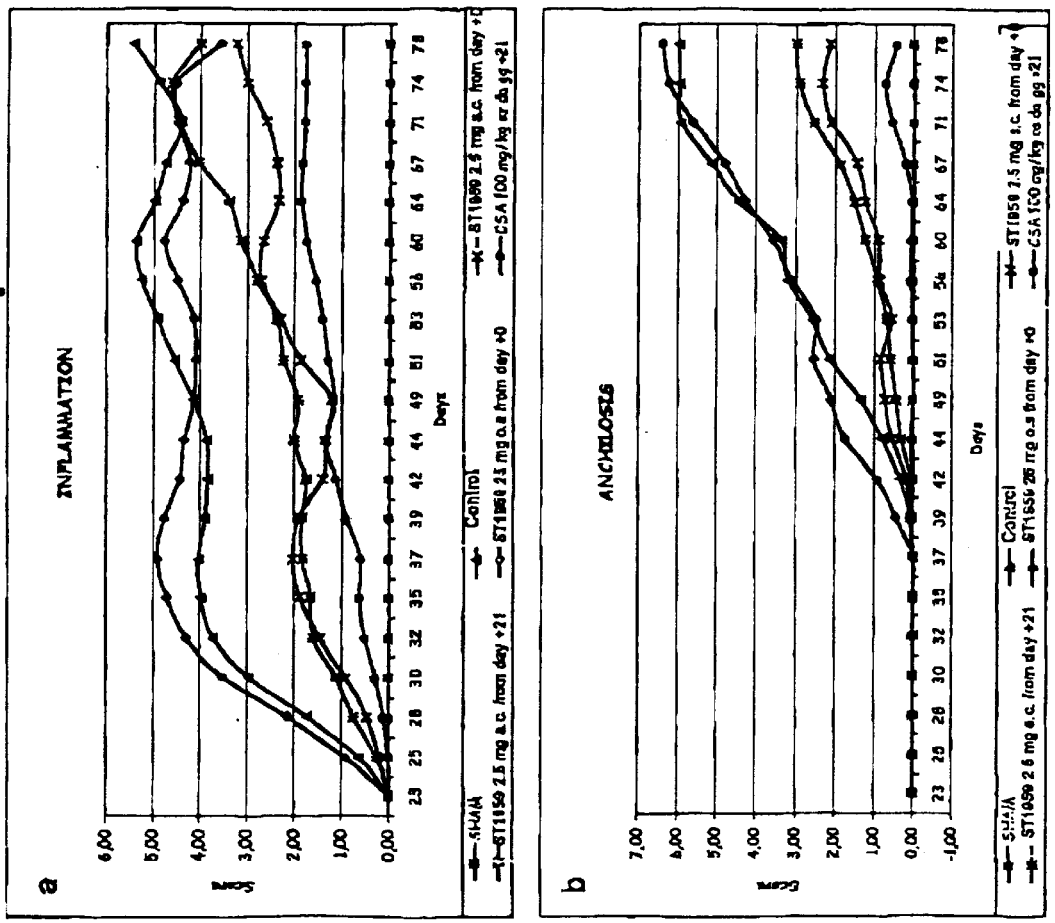
Figure 6: ST1959 improves RA

USE OF 3-(2-ETHYLPHENYL)-5-(3-METHOXYPHENYL)-1H-1,2,4-TRIAZOLE FOR THE TREATMENT OF AUTOIMMUNE DISEASES

The present invention relates to a method for the treatment of autoimmune diseases, which are effectively treated by administering the compound 3-(2-ethylphenyl)-5-(3-methoxyphenyl)-1H-1,2,4-triazole.

BACKGROUND OF THE INVENTION

Multiple sclerosis (MS) is an inflammatory demyelinating disease of the central nervous system (CNS) that is thought to be mediated by an autoimmune attack directed against CNS myelin antigens. Based on animal models, as well as on data gathered from analyses of leukocytes and tissues from patients with MS, antigen specificity is considered to reside within T cells expressing the $\alpha\beta$ T cell receptor (TCR), with encephalitogenic activity dependent on the expression of a cytokine profile characteristic of a Th1-type phenotype: interferon-gamma (IFN$\gamma$), lymphotoxin (LT) and tumor necrosis factor-alpha (TNF$\alpha$). T cells that express a Th2-type cytokine profile (IL-4, IL-5 and IL-13) or regulatory cytokines such as transforming growth factor-beta (TGF$\beta$) and IL-10, are thought to interfere with this process by blocking the acquisition of the Th1-phenotype and/or by blocking the downstream targets of effector cytokines, such as the activation of macrophages.

The critical nature of the cytokine profile of the antigen-reactive $\alpha\beta$ T cells to disease expression raises the question as to the nature of the antigen recognition process that results in the acquisition of these specific cytokine profiles. Although it has been known for some time that the presence of adjuvants and the route of antigen presentation are important determinants of encephalitogenic activity in animals, how these processes shape the nature of the acquired immune response, as well as the contribution of other non-antigen-specific leukocyte populations, have only recently started to come into sharper focus with an expanding recognition of the different cell populations that function at the interface between the innate and acquired immune response.

The innate immune response functions as a first line of defense against a wide range of infectious and toxic agents. Historically, this response has been attributed to cells with phagocytic activity, such as macrophages and polymorphonuclear cells, and/or potent cytotoxic activity, such as natural killer cells (NK cells), mast cells and eosinophils. The activity of these different cell populations is aided and abetted by a number of different soluble molecules collectively known as acute phase proteins, such as the interferons, specific components of the complement cascade and cytokines, that serve to enhance phagocytic and cytotoxic activity, as well as lead to the accumulation of these cells at sites of tissue injury. If these first lines of defense are breached, then activation of the adaptive immune response ensues, leading to the formation of a specific immune response that may display anyone of a number of different characteristics. The generation of this acquired immune response is an exclusive property of lymphocytes.

More recently, however, it has become recognized that minor subpopulations of lymphocytes may also function as part of the innate immune response. Although it is likely that the complete functional role of these specialized subsets of lymphocytes remains poorly understood, current interest in them has focused on their role in defining the cytokine milieu at sites of tissue injury, influencing the nature of the adaptive immune response that is generated. Thus, many of these studies have focused on the role of IFN$\gamma$ and IL-12 in defining a Th1-type cytokine profile and IL-4 a Th2-type cytokine profile. Subpopulations of all of the three major groups of lymphocytes, $\alpha\beta$ T cells, $\gamma\delta$ T cells and B cells, likely fall into this category. These lymphocyte populations are characterized by the use of a highly conserved antigen receptor complexes, expression of additional pattern-recognition receptors, such as members of the Toll-like receptor family or receptors normally detected on NK cells, and the rapid release of high levels of cytokines and chemokines following interaction with specific ligands.

$\gamma\delta$ T cells: T cells expressing the $\gamma\delta$ T cell receptor (TCR) constitute a minor population of the total circulating T cell population. In common with $\alpha\beta$ T cells, $\gamma\delta$ T cells express a rearranged TCR, but the mechanisms involved in the acquisition of TCR diversity, as well as the nature of the antigens recognized, are clearly different (Chien Y. H. et al. *Annu. Rev. Immuniol.* 1996;14:511–32). Analysis of CDR3 length distributions, as well as crystallographic studies, have suggested greater structural similarity of the $\gamma\delta$ TCR to immunoglobulin heavy chain genes, lending further support to the conclusion that the molecular nature of antigen recognition by $\gamma\delta$ T cells is fundamentally different from that utilized by $\alpha\beta$ T cells. $\gamma\delta$ T cells also differ from $\alpha\beta$ T cells in that most $\gamma\delta$ T cells coexpress receptors found on natural killer cells (NK—R) (Battistini L. et al.; *J. Immunol.* 1997;159:3723–30). Expression of these receptors on T cells has been shown to modulate several T cell functions including cytotoxicity, cytokine release and transendothelial cell migration (Reyburn H. et al., *Immunol. Rev.* 1997;155:119–25) These data indicate that the regulation of $\gamma\delta$ T cell function is likely to be different from that found in most $\alpha\beta$ T cells, involving activation (or inhibition) by signaling through both the TCR and NK—R. It has been suggested that NK—R functions as costimulatory molecules that are exquisitely responsive to changes in cell surface expression of MHC modulated by infection or to the activation state of the cells (Reyburn H. et al., *ibid.*).

In healthy adults the majority of $\gamma\delta$ T cells express a TCR that utilizes the V$\gamma$9V$\delta$2 gene segments The expansion of this specific population of $\gamma\delta$ T cells is thought to be due to a response to non-protein bacterial antigens such as pyrenil-pyrophosphate derivatives and other components of bacterial cell walls, without classical MHC-restriction (Salerno A et al., *Crit. Rev. Immunol.* 1998;18:327–57)). The response to these types of antigens has been found to be critically dependent upon the use of germline encoded lysine residues in the J$\gamma$1.2 segment (Miyagawa F. et al., *J. Immunol.* 2001;167:6773–6779). Thus, although the response to phosphate antigens may be polyclonal in nature, conserved elements are used by the responding cells. Conserved sequences of $\gamma\delta$ T cell receptor have been noted in cells and/or tissues isolated from patients with MS, suggesting a response to a common antigen.

$\gamma\delta$ T cells share many features in common with the $\alpha\beta$TCR+NK-T cells, including the expression of NK receptors, constitutive expression of the IL-2r$\beta$, usage of highly conserved TCR sequences and restriction, at least for some subsets, by CD1 molecules (Spada F. M. et al, *J. Exp. ed.* 2000;191:937–48). This would suggest that some $\gamma\delta$ T cells may provide a similar link between the innate and acquired immune response (Poccia F. et al., *Immunol. Today* 1998;19:253–6). Consistent with such a notion is that activation of V$\delta$2+ T cells with phosphate antigens has been shown to lead to the rapid release of large amounts of both cytokines and chemokines (Poccia F. et al., *J. Immunol.* 1997;159:6009–17; Cipriani B. et al, *Blood* 2000;95:39–47). Interestingly, there are accumulating data that suggest that V region usage may implicate specific subsets of γδ T cells in mediating Th1 or Th2-type responses—with Vδ2+ cells showing a Th1-type bias and Vδ1+ cells a Th2-type bias. So for example, it has been shown that γδ T cells in MS lesions express a predominantly Vδ2 phenotype (Battistini L. et al., *Mol. Med.* 1995;1:554–62) and that Vδ2 cells in the peripheral blood of patients with MS show evidence of activation. In the CSF, however, Vδ1 cells are the predominant γδ T cell population (De Libero G., *Springer Semin. Immunopathol.* 2000;22:219–38)

Studies that have examined a potential role for γδ T cells in demyelinating diseases further support the conclusion that although γδ T cells show evidence of activation in patients with either MS or Gulllain Barrè syndrome (GBS), differences exist in the phenotypic and functional properties of these cells in the two diseases In particular, the data indicate that in patients with MS the Vδ2 subset is activated and that these cells can be induced to secrete high levels of proinflammatory cytokines.

Once activated via the TCR, γδ T cells may also function as NK cells, responding in either a positive or negative fashion to NK cell targets (Battistini L. et al., *J. Immunol.* 1997;159:3723–30; De Libero G. *Microbes Infect.* 1999;1:263–7) Furthermore, in MS patients with active disease, the percentage of circulating Vδ2+ T cells coexpressing NKRP1A (the human homologue of NK1.1) has been found to be significantly increased compared with healthy donors. When Vδ2+ and Vδ1+ T cells were sorted from MS patients and healthy volunteers and cloned, all Vδ2+ clones expressed NKRP1A. NKRP1A was strongly up-regulated on Vδ2+ cells by culture with IL-12 whereas no up-regulation of NKRP1A by IL-12 was noted on Vδ1+ clones. In transendothelial migration assays, Vδ2+ NKRP1A+ clones migrated more effectively than Vδ1+ clones, and this migratory potential was enhanced following culture with IL-12. Migration was strongly inhibited by the F(ab')2 of an anti-NKRP1A antibody, suggesting that this receptor for common lectins is involved in the transendothelial cell migration process. It was also shown that in freshly isolated PBMC from MS patients, the migrated population was enriched in Vδ2+ NKRP1A+ cells. Thus the expression of NKRP1A on Vδ2+ cells is associated with an increased ability to migrate across the vascular endothelium, an activity that may be upregulated by IL-12 present in the microenvironment (Poggi A. et al., *J. Immunol.* 1999;162:4349–54). Taken together, these data suggest that γδ T cells could be rapidly recruited to sites of inflammation in the CNS where they could significantly contribute to the cytokine/chemokine balance of the lesion, as has been demonstrated in EAE (Spahn T. W. et al, *Eur. J. Immunol.* 1999;29:4060–71, Rajan A. J. et al., *J. Immunol.* 2000;164:2120–30).

Accordingly the availability of a compound having immunomodulatory properties on the innate immune response of effector γδ+ T cells would be of great benefit to the subjects in need thereof.

BRIEF DESCRIPTION OF THE INVENTION

The present invention is further explained with reference to the attached drawings in which:

FIG. 1 is a bar graph showing the compound of the present invention (ST1959) inhibits, in dose-like manner, the expansion of Vδ2 T cells when cultured with IPP;

FIG. 2 is a series of four histograms showing ST1959 is not toxic to Vδ2 T cells, at various doses against a control (CTRL);

FIG. 3 is a bar graph showing ST1959 at various doses inhibits IFNγ release in IPP-stimulated T cells;

FIG. 4 is a bar graph showing the effect of ST1959 inhibits IFNγ producing Vδ2 T cells following stimulation with IPP provides a net reduction in a dose dependent manner;

FIG. 5a is a graph showing ST1959 (■) against vehicle/carrier (x) as ST1959 controls renal damage as it relates to an average of the number of animals with urinary proteins in the two groups (■ and x);

FIG. 5b is a graph reporting the score of urinary leucocytes over a period of several weeks for ST1959 (■) and a blank (vehicle only x);

FIG. 5c is a graph showing the survival of animals as treated in Example 2 for those treated with ST1959 (■) related to the untreated animals (x) vehicles only);

FIG. 5d is a graph showing ST1959 did not effect the body weight of untreated animals;

FIG. 6a is a graph showing ST1959 improves animals with collagen induced arthritis by reducing inflammation; and FIG. 6b is a graph showing ST1959 reduces anchilosis in animals with collagen induced arthritis.

SUMMARY OF THE INVENTION

It has now been found that a compound of the 3,5-diaryl-s-triazoles class of molecules, more precisely 3-(2-ethylphenyl)-5-(3-methoxyphenyl)-1H-1,2,4-triazole (hereinafter also called ST1959) efficiently treats autoimmune diseases. It has also been found that the compound according to the present invention inhibits the γδ T cell effector response by a non-cytotoxic mechanism.

Accordingly, it is an object of the present invention a method for treating a subject affected by an autoimmune disease comprising administering to said subject an effective amount of 3-(2-ethylphenyl)-5-(3-methoxyphenyl)-1H-1,2,4-triazole.

In particular, according to the method of the present invention, said subject is affected by an autoimmune disease, such as multiple sclerosis, lupus erythematosus sistemicus, arthritis reumatoid (RA).

In another aspect of the present invention, it is a further object of the present invention a method for inhibiting γδ T cells in a subject in need thereof, said method comprising administering to said subject an effective amount of 3-(2-ethylphenyl)-5-(3-methoxyphenyl)-1H-1,2,4-triazole.

In a preferred embodiment of the present invention, said subject is a mammal, more preferably a human.

3-(2-ethylphenyl)-5-(3-methoxyphenyl)-1H-1,2,4-triazole was described in U.S. Pat. No. 4,379,155, issued on 5 Apr. 1983, as part of a large family of 1,2,4-triazoles with anti-fertility activity. This compound was thoroughly studied as anti-fertility agent (Galliani et al. *Pharm. Dyn.* 5, 55–61 (1982)). Later, U.S. Pat. 6,323,230, assigned to Geange Ltd., issued on 27 Nov., 2001, discloses a large family of nitrogen heterocyclic aromatic derivatives useful for the topical treatment of the epithelial tissues diseases, in particular psoriasis, atopic dermatitis, ulcerative colitis and Crohn's disease and the administration routes are epicutaneous, oral and rectal. According to the disclosure of the above mentioned U.S. Pat. 6,323,230, the oral route is to be understood as an oral formulation suitable for delivering the compound specifically at the site of action, namely at the epithelial mucosae of the low intestine. In fact, the oral route, when considered for the original anti-fertility activity, isn't the right choice with respect to the parenteral injection (Gallani et al. *Pharm. Dyn.* 5, 55–61 (1982)), due to a rapid and extensive hepatic first-pass effect leading to the formation of inactive metabolites (Assandri A. et al *Drug Interactions*, IV, 237–261 (1982); Assandri A. et al *Xenobiotica* 14, 429–433 (1984)). The same reference teaches that the compound according to the present invention does not retain hormonal or anti-hormonal or lympholytic activity, inhibits the antibody formation versus corpuscolar antigens (ram erythrocytes) when administered after the agents, does not exert a selective action on lymphocytes B and/or T and does not interfere with the macrophagic function and does not retain cytotoxic activity. The immunological profile of the compound was described in Mistrello G. et al., *Immunopharmacology*, vol 10, 1985, 163–169. In this reference, the compound of the present invention showed to be inactive in treating arthritis.

The compound of the present invention has inhibitory activity on γδ T cells, therefore, is useful in the treatment of diseases which are effectively treated by administering a compound inhibiting γδ T cells.

The administration of the compound of the present invention is made by means of conventional pharmaceutical compositions, for example, as disclosed in the above mentioned U.S. Pat. Nos. 4,379,155, 6,323,230. The preferred route of administration, although not exclusive, is the subcutaneous one.

The following examples further illustrate the invention.

EXAMPLE 1

Multiple Sclerosis

Blood samples were obtained from 18 healthy volunteers and from 18 patients with clinically active MS in the relapsing phase or in the first episode of disease, with abnormal magnetic resonance imaging brain scan; none had received immunosuppressive treatment for at least 3 months before entering the study. Patients and 18 healthy donors were matched for sex and age.

Peripheral and cord blood mononuclear cells were isolated from heparinized blood by Ficoll-Hypaque (Pharmacia Biotech, Uppsala, Sweden) and cultured at $1.5 \times 10^6$ cells/ml in complete medium (RPMI 1640, 10% v/v heat-inactivated FCS, 2 mM L-Glutamine, 10 U/ml penicillin/streptomycin) PBMC from control donors or MS patients were stimulated in vitro for 9 days in the presence of 30 μM isopentyl pyrophosphate (IPP; Sigma-Aldrich, St. Louis, Mo.) and 50 U/ml rIL-2 (Boehringer Mannheim, Mannheim, Germany). After 3 days of culture, the volume corresponding to half-culture supernatant was replaced by complete medium with rIL-2. The expansion of Vγ9Vδ2+ T cells after 6 days of culture was determined by cytometric analysis using double staining with anti-CD3 and anti-TCR-Vδ2 mAbs coupled to PE or FITC, respectively. Vδ2 expansion index was calculated dividing the absolute number of Vδ2+ T cells in stimulated cultures by the absolute number of Vδ2+ T cells in unstimulated cultures.

Cytokine production was detected by flow cytometric analysis as previously described. Human PBMC were stimulated for 6 h with IPP (100 μM; Sigma-Aldrich) and/or 100 U/ml rIL-2 (Boehringer Mannheim). Brefeldin A (10 μg/ml) was added 1 h after stimulation to block intracellular transport allowing cytokine accumulation in the Golgi. Cells were washed twice in PBS, 1% BSA, and 0.1% sodium azide and stained with mAbs specific for the membrane Ags described above for 15 min at 4° C. Samples were then fixed in 1% paraformaldehyde for 10 min at 4° C., incubated with anti-IFN-mAb diluted in 1×PBS, 1% BSA, and 0.5% saponin. The cells were finally washed twice in 1×PBS, 1% BSA, 0.1% saponin, and acquired on a FACScan (BD Biosciences). Control for nonspecific staining was monitored with isotype-matched mAbs and nonspecific staining was always subtracted.

IFN-γ levels were determined by a standard sandwich ELISA as previously described. Antibodies and standards were purchased from PharMingen. Enhanced protein-binding ELISA plates (Nunc Maxisorb; Nunc Man Corp., Roskilde, Denmark) were used.

A rather unique feature of the Vγ9Vγ2 TCR is its ability to recognize both naturally occurring and synthetic non-peptidic phosphoantigens. These antigens can be found in pathogenetic microorganisms such as Plasmodium, Francisella, and Mycobacterium. One of these is isopentyl pyrophosphate (IPP), a 246-Da molecule that has a five-carbon isoprenyl chain and a pyrophosphate moiety. Following activation by these compounds, Vγ9Vδ2 cells expand and rapidly secrete proinflammatory cytokines such as TNF-α and IFN-γ and acquire potent cytotoxic activity, implicating these cells as important mediators of inflammation at sites of Ag recognition. It is known that IPP exclusively stimulates proliferation of the Vδ2Vγ9 T-cell subset and also induces cytokine production in the same γδ T-cell population. To determine whether 3-(2-ethylphenyl)-5-(methoxyphenyl)-1H-1,2,4-triazole inhibits Vδ2 T cell expansion following IPP stimulation, freshly isolated PBMCs from healthy donors or MS patients were cultured with either IL-2, IL-2 +IPP, or IL-2 +IPP+3-(2-ethylphenyl)-5-(3-methoxyphenyl)-1H-1,2,4-triazole (30 μM or 60 μM) and Flow Cytometric analysis was performed at day 6 after stimulation to determine the percentage of cells present in the culture that expressed the Vδ2 gene product. The compound of the present invention efficiently inhibited, in a dose response manner, the expansion of Vδ2+ T cells when cultured together with IPP (FIG. 1). The percentages of inhibition of the expansion were 39% and 38%, respectively, when the compound was used at the concentration of 30 μM in cells isolated from MS patients or from healthy individuals. A difference was noted in the inhibition caused by 3-(2-ethylphenyl)-5-(3-methoxyphenyl)-1H-1,2,4-triazole at higher concentration (60 μM) in the two groups studied, 71% of inhibition was found in cells isolated from MS patients versus 88% in cells from healthy individuals.

To determine whether the compound of the present invention was toxic for Vδ2 T cells, unfixed cells were stained with PI to assess cell membrane integrity and were analyzed by Flow Cytometry. In cells cultured for 6 days with IL-2 alone 5,96% cells were PI+, whereas cells challenged with IPP+ IL-2 showed 9,66% of PI+ cells. When ST1958 (30 μM or 60 μM) was added PI+ cells were respectively 15% and 17,65% (FIG. 2). The little increase PI+ dead cells in the cultures where 3-(2-ethylphenyl)-5-(3-methoxyphenyl)-1H-1,2,4-triazole was added compared with that with IPP alone demonstrate that this compound lead to a robust inhibition of Vδ2 T cell expansion following IPP stimulation (56% of inhibition at 30 μM and 91% inhibition at 60 μM) by a non-cytotoxic mechanism.

To determine whether 3-(2-ethylphenyl)-5-(3-methoxyphenyl)-1H-1,2,4-triazole inhibited the release of proinflammatory mediators by Vδ2 T cells activated with phosphate Ags, PBMCs were activated with IPP (30 μM) in the presence or the absence of the compound at 30 μM and 60 μM, and the release of IFN-γ was determined by ELISA 24 h post-stimulation. The presence of the compound in the medium potently inhibited the release of IFN-γ from these cells in a dose-dependent manner (55% and 65% of inhibition when the compound at 30 μM was added in the cells isolated from MS and healthy donors respectively; 74% and 82% of inhibition when the compound at 60 μM was added in the cells isolated from MS and healthy donors respectively—FIG. 3).

The effect of 3-(2-ethylphenyl)-5-(3-methoxyphenyl)-1H-1,2,4-triazole was tested on the induction of Vδ2+ IFN-δ+ cells T cells following stimulation for 6 h with IPP. These data show that the compound of the invention determines a net reduction in a dose dependent manner of the number of Vδ2+ T cells producing IFN-γ following stimulation with IPP.

3-(2-ethylphenyl)-5-(3-methoxyphenyl)-1H-1,2,4-triazole used at a concentration of 30 μM leads to inhibitions of 50% and 25% of the Vδ2+ IFN-γ+ cells induced by IPP in cells isolated from healthy donors and MS patients, respectively. On the contrary the level of inhibition found with 60 μM of the compound was similar for the two group of patients: 93% of inhibition of the Vδ2+ IFN-δ+ cells induced by IPP in cells isolated from healthy donors and 92% in cells isolated from MS patients (FIG. 4).

3-(2-ethylphenyl)-5-(3-methoxyphenyl)-1H-1,2,4-triazole has inhibitory effects on γδ T cells from both MS patients and healthy individuals. In all situations tested there is a slight—but significant—difference in the inhibitory effects exploited on cells derived from MS patients compared to those derived from healthy individuals, in that inhibition of γδ T cell function is more effective in healthy subjects. Poggi, A. et al., *J. Immunol.* 162:4349 have previously described that γδ T cells in MS patients are more activated than those derived from healthy individuals, as they express molecules which are critical for interaction with endothelium and thus can readily migrate in inflamed tissue amplifying the inflammatory response which underlies demyelination and, consequently, neurological disfunction. It is conceivable that inhibition of a pre-activated cell is more arduous than that of a resting population, since it requires the shutting off of cellular mechanisms which have already been initiated. Nevertheless, in most assays inhibition of γδ T cell function in MS patients reached 60–70%. Given the wide distribution of the Ags recognized by these Vγ9Vδ2+ T cells and the rapidity with which proinflammatory cytokines such as IFN-γ and TNF-α and chemokines such as MIP-1α and MIP-1β are produced through pathways that appear to differ from αβ T cells, these cells could play an important role in the transition from the innate to the acquired immune response by biasing reactions toward a Th1-type response. This would suggest that at sites of Ag recognition 3-(2-ethylphenyl)-5-(3-methoxyphenyl)-1H-1,2,4-triazole could effectively inhibit γδ T cell activation, which could have broad implications for the activation of both innate and acquired immune responses.

EXAMPLE 2

Lupus

Mice MRL/lpr (female) of about 6 weeks were obtained from Jackson (USA). These mice spontaneously develop a Lupus like pathology around the 8th week. ST1959 administration was started at the 6th week and performed s.c. twice/week 2.5 mg/kg in 0.1 ml of sesame oil. One group of treated and one group of control (sesame oil) were included in the study (12 mice/group). Once a week the renal damage was monitored by detecting proteinuria and urinary leucocytes. Data reported in the FIG. 5a represent the average of the % of animals with urinary proteins higher than 100 mg/dl in the two groups. Panel b indicate the score of urinary leucocytes (score 0–3). All determinations were performed by the use of Multistix 10SG (SU). Panel c shows the % of survival of the two groups and indicates a delay in start of mortality for the ST1959 treated animals compared to control group and a higher overall survival with 60 and 25%, respectively. The administration of ST1959 did not affect the body weight of treated animals as shown in panel d, thus suggesting lack of toxicity.

EXAMPLE 3

Collagen Induced Arthritis

Mice DBA/1 J were obtained from Charles Rivers (Italy). Induction of arthritis was performed by administration, at day 0 and +21 of 100 μl/mouse i.d. of emulsions composed of equal volumes of Complete Freund's adjuvant +2 mg/ml of *M. tubercolosis* and 4 mg/ml of bovine type II collagen. Mice were randomly assigned to study groups (8 mice/group) including; ST1959 o.s. treated, cyclosporin (CSA) o.s. treated, vehicle (sesame oil). Sham mice were treated with emulsion lacking the collagen and did not receive further administrations. The compounds were administered 3 times/week s.c. or o.s. in 0.1 ml of sesame oil starting from day 0 or day +21. The scores of inflammation and anchilosis was between 0–3 for each limb. As shown in FIG. 6, the ST1959 s.c. treatment significantly reduced both inflammation (6a) and anchilosis (6b). On the contrary, the oral administration did not produce any therapeutic effect. The s.c. dose of ST1959 was $1/1500$ of its $LD_{50}$. Cyclosporine treatment, at a very high dose (100 mg/kg), was included as the positive control.

What is claimed is:

1. A method for treating an autoimmune disease selected from the group consisting of multiple sclerosis, lupus erythematosus systemicus and reumatoid arthritis in a subject in need thereof, comprising administering to said subject an effective amount of 3-(2-ethylphenyl)-5-(3-methoxyphenyl)-1H-1,2,4-triazole.

2. The method according to claim 1, wherein said subject is a mammal.

3. The method according to claim 1, wherein said subject is a human.

4. A method for inhibiting γδ T cells in a subject in need thereof, said method comprising administering to said subject an effective amount of 3-(2-ethylphenyl)-5-(3-methoxyphenyl)-1H-1,2,4-triazole.

5. The method according to claim 4, wherein said subject is a mammal.

6. The method according to claim 4, wherein said subject is a human.

* * * * *